(12) United States Patent
Zhang et al.

(10) Patent No.: US 10,279,050 B2
(45) Date of Patent: May 7, 2019

(54) SUCROSE ESTER BASED CATIONIC GENE VECTOR AND PREPARATION METHOD THEREOF

(71) Applicant: DALIAN NATIONALITIES UNIVERSITY, Dalian, Liaoning (CN)

(72) Inventors: Shubiao Zhang, Liaoning (CN); Defu Zhi, Liaoning (CN); Shaohui Cui, Liaoning (CN); Yinan Zhao, Liaoning (CN); Quan Zhou, Liaoning (CN)

(73) Assignee: DALIAN NATIONALITIES UNIVERSITY, Dalian, Liaoning (CN)

( * ) Notice: Subject to any disclaimer, the term of this patent is extended or adjusted under 35 U.S.C. 154(b) by 81 days.

(21) Appl. No.: 15/546,942

(22) PCT Filed: Jun. 25, 2015

(86) PCT No.: PCT/CN2015/082263
§ 371 (c)(1),
(2) Date: Jul. 27, 2017

(87) PCT Pub. No.: WO2016/127543
PCT Pub. Date: Aug. 18, 2016

(65) Prior Publication Data
US 2017/0326255 A1 Nov. 16, 2017

(30) Foreign Application Priority Data
Feb. 11, 2015 (CN) .......................... 2015 1 0071065

(51) Int. Cl.
| | | |
|---|---|---|
| *A61K 48/00* | (2006.01) | |
| *C07H 1/00* | (2006.01) | |
| *C07H 13/06* | (2006.01) | |
| *C07J 17/00* | (2006.01) | |
| *A61K 9/107* | (2006.01) | |
| *A61K 9/127* | (2006.01) | |
| *A61K 47/26* | (2006.01) | |
| *A61K 47/28* | (2006.01) | |
| *C07H 5/02* | (2006.01) | |
| *C12N 15/113* | (2010.01) | |
| *C12N 15/88* | (2006.01) | |
| *C12N 15/11* | (2006.01) | |

(52) U.S. Cl.
CPC ........ *A61K 48/0033* (2013.01); *A61K 9/1075* (2013.01); *A61K 9/127* (2013.01); *A61K 9/1272* (2013.01); *A61K 47/26* (2013.01); *A61K 47/28* (2013.01); *C07H 1/00* (2013.01); *C07H 5/02* (2013.01); *C07H 13/06* (2013.01); *C07J 17/005* (2013.01); *C12N 15/113* (2013.01); *C12N 15/88* (2013.01); *C12N 15/111* (2013.01); *C12N 2310/14* (2013.01); *C12N 2320/32* (2013.01)

(58) Field of Classification Search
CPC ... A61K 48/0033; A61K 9/1075; A61K 9/127
See application file for complete search history.

(56) References Cited

U.S. PATENT DOCUMENTS

| | | | |
|---|---|---|---|
| 2008/0171721 A1* | 7/2008 | Memarzadeh | ......... C07H 13/02 514/53 |
| 2009/0074935 A1 | 3/2009 | Lee | |

FOREIGN PATENT DOCUMENTS

| | | |
|---|---|---|
| CN | 1844402 | 10/2006 |
| CN | 101560228 | 10/2009 |
| CN | 102417527 | 4/2012 |
| CN | 103553970 | 2/2014 |
| WO | WO2004104016 | 12/2004 |
| WO | WO2006016097 | 2/2006 |

OTHER PUBLICATIONS

Felgner et al., "Lipofection: A highly efficient, lipid-mediated DNA-transfection procedure", PNAS 1987, 84:7413-7417.
Ye et al., "Effects of Particle Size of Sucrose Suspensions and Pre-incubation of Enzymes on Lipase-Catalyzed Synthesis of Sucrose Oleic Acid Esters", J. Am. Oil Chem. Soc. 2014, 91: 1891-1901.
International search report dated Nov. 3, 2015 from corresponding application No. PCT/CN2015/082263.

* cited by examiner

*Primary Examiner* — Pancham Bakshi
(74) *Attorney, Agent, or Firm* — Hauptman Ham, LLP (57) ABSTRACT

The invention provides a class of sucrose ester based cationic lipids and preparation method thereof. The vector prepared using the cationic lipid can be used to deliver nucleic acid. The sucrose ester based cationic lipid is prepared by using a chemical synthesis method in the invention, wherein the synthesis method is simple, and has a relatively high product yield. A composition, including suspension, emulsion, micelle and liposome and the like, can be prepared by mixing the sucrose ester based cationic lipid compound of the invention with a co-lipid. Sucrose ester based cationic lipid complex can be prepared by using the said composition and nucleic acid, which has advantages such as simple preparation, low toxicity and high transfection efficiency, and is a novel and highly efficient gene vector.

8 Claims, 4 Drawing Sheets

Size (nm)
Fig 4

SUCROSE ESTER BASED CATIONIC GENE VECTOR AND PREPARATION METHOD THEREOF

RELATED APPLICATIONS

The present application is a National Phase of International Application Number PCT/CN2015/082263, filed Jun. 25, 2015, and claims the priority of China Application No. 201510071065.X, filed Feb. 11, 2015.

FIELD OF THE INVENTION

The present invention belongs to the technological field of biological medicine, which relates to a class of sucrose ester based cationic lipid compounds and preparation methods thereof. The compounds can be used to prepare sucrose ester-based cationic lipid compositions and complexes, and used for nucleic acid delivery.

BACKGROUND hi recent years, many new methods have been invented to treat diseases, however there is still no efficient method to cure diseases such as cancer. Furthermore, gene therapy, as a brand new and revolutionary treatment method, is a potential way to cure intractable diseases such as cancer, angiocardiopathy and congenital immune deficiency, etc. However, the core technology—gene delivery problem always limits the development of gene therapy and clinical trials for a long time, wherein it is undoubtedly crucial for the success of gene therapy to obtain a highly efficient and safe gene vector.

At present, gene transport vectors used globally are mainly divided into two categories: one is viral vector and the other is non-viral vector. The viral gene vector is a vector using the ability of the virus to infect cells, based on the virus to build a vector for carrying gene, and accordingly, the vector that delivers genes not using virus is collectively referred to as non-viral gene vector. Although the viral gene vector has the advantage of high efficiency for gene transport, it has the disadvantages such as high immunogenicity, small capacity, variability and carcinogenicity, etc. However, the non-viral gene vector opens up a new path for gene therapy with its advantages, namely design flexibility, low toxicity, low immunogenicity, low tumorigenesis, easy preparation and capable of achieving cell-specific expression and long-term gene expression. So far, nearly one-third of more than 2,000 cases of the clinical trials of gene therapy have been carried out via non-viral gene vectors. However, there is a certain difference between the transfection efficiency of non-viral gene vector and that of the viral vectors, which is a bottleneck restricting its clinical trials. Developing the non-viral gene vector with high efficiency and low toxicity has become one of the important research topics of gene therapy.

Cationic liposomes as a class of non-viral gene vectors, because of their advantages such as simple preparation, non-immunogenicity, capable of repeating transfection, and easy commercialization, etc., have been rapidly developed in recent years. In 1987, Felgner, et al. (PNAS 1987, 84:7413-7417) for the first time prepared a cationic liposome from a cationic lipid DOTMA to deliver DNA, which pioneered the cationic liposome in the field of gene therapy. The liposome formed by the cationic lipid has a similar structure to that of a biomembrane, and can package an exogenous gene as a vector. Cationic liposomes which are positively charged at a physiological pH, can be self-assembled with negatively charged phosphate groups in a nucleic acid molecule to form liposome/gene complexes by means of an electrostatic interaction, the complexes can be adsorbed on the cell surface by the electrostatic interaction, and thereby introduce the exogenous genes into cells through cell endocytosis or other actions so as to play a therapeutic role of genes. Since 1987, many cationic lipids have been designed and synthesized for nucleic acid delivery (Focus 1993, 15:73-83). However, the existing cationic lipids have high toxicity and their transfection efficiency needing to be improved.

It is well known that carbohydrate compounds are widely distributed in nature with high safety. Sucrose ester prepared by using sucrose as a starting material can form a vesicular or double lamellar structure in the aqueous phase, with good biocompatibility and degradability. However, due to a large number of hydroxyl groups in sucrose, it is difficult to obtain single-structure sucrose ester compound by a chemical synthesis method (J. Am. Oil Chem. Soc. 2014, 91: 1891-1901.). So far, there is no relevant research work about applying sucrose ester-based gene vectors for gene delivery. Therefore, the research and development of sucrose ester based gene vector with good biocompatibility, high efficiency and low cytotoxicity have important scientific significance and economic values for developing gene vectors with independent intellectual property rights.

SUMMARY OF THE INVENTION

The objective of the invention is to provide a class of safe and highly efficient sucrose ester based cationic gene vectors and preparation method thereof, which mainly comprises a class of sucrose ester based cationic lipid compounds and preparation method thereof, a class of sucrose ester based cationic compositions and preparation method thereof, and a class of sucrose ester based cationic lipid complexes and preparation method thereof.

Unless otherwise indicated, the terms used herein have the following meanings.

The term "hydroxyl" as used herein includes alkyl, alkenyl and alkynyl.

The term "alkyl" as used herein includes linear-chain alkyl and branched-chain alkyl. For example, "$C_{1-4}$ alkyl" includes methyl, ethyl, n-propyl, isopropyl, n-butyl and t-butyl. Similar rules are also applicable to other groups used in the invention.

The term "halogen" as used in the invention includes fluorine, chlorine, bromine and iodine.

Figure 1:
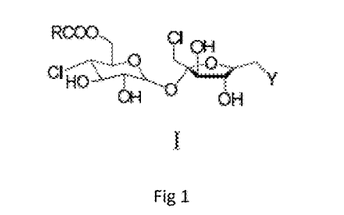
FIG. 1 is a structural formula I of a sucrose ester based cationic lipid compound of the invention.
Figure 2:
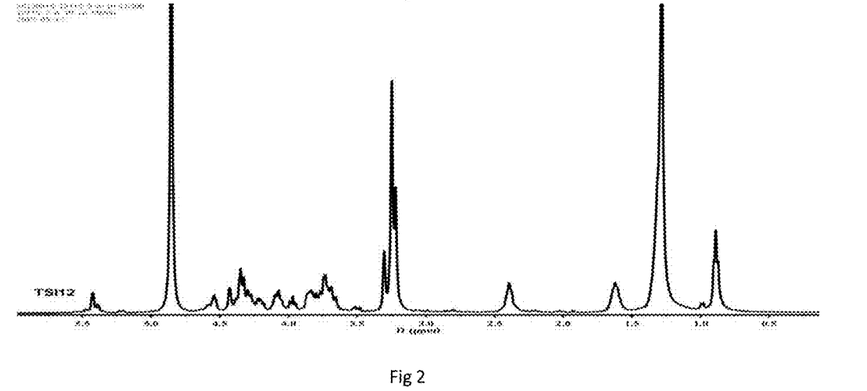
FIG. 2 is the $^1H$ NMR spectrum of Example 1.
Figure 3:
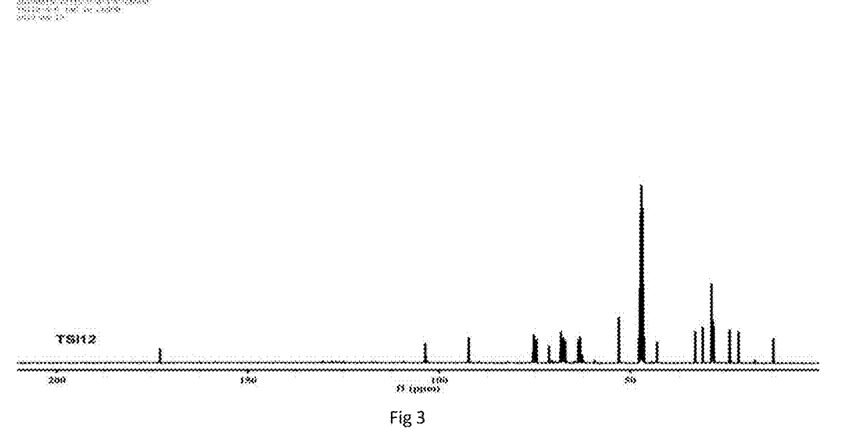
FIG. 3 is the $^{13}C$ NMR spectrum of Example 1.

I. The sucrose ester based cationic lipid compound of the invention has a structure of a general formula I:

Wherein,

R is selected from $C_{10\text{-}20}$ hydroxyl ester, bile acid group and cholesterol ester group;

Wherein said cholesterol ester group (B1) has the following structure:

In a preferred technical solution, R is preferably selected from $C_{12-18}$ alkyl ester, octadecenyl ester ($C_{17}H_{34}COO-$), bile acid group and cholesterol ester group. More preferably, R is selected from $C_{12}$ alkyl ester, $C_{14}$ alkyl ester, octadecenyl ester ($C_{17}H_{34}COO-$) and cholesterol ester group.

Y is selected from $-NR^aR^b$ and $-N^+R^aR^bR^cX^-$, wherein $R^a$, $R^b$ and $R^c$ are the same or different, and are selected from hydrogen, $C_{1-6}$ hydroxyl, $C_{1-6}$ hydroxyalkyl, galactosyl, mannosyl and/or folic acid ester group; $X^-$ is selected from $F^-$, $Cl^-$, $Br^-$ and $I^-$. In a preferred technical solution, Y is preferably selected from $NR^aR^b$, wherein $R^a$ and $R^b$ are preferably selected from $C_{1-6}$ alkyl, $C_{1-6}$ hydroxyalkyl, $C_6H_{11}O_6-$ (galactosyl), $C_6H_{11}O_6-$ (mannosyl) and folic acid ester group ($C_{18}H_{18}N_7O_4COOCH_2CH_2-$); more preferably, $R^a$ and $R^b$ are selected from methyl, ethyl, hydroxymethyl, hydroxyethyl, galactosyl and folic acid ester group; wherein the galactosyl (B2), the mannosyl (B3), and the folic acid ester group (B4) have the following structures:

II. The preparation method of the above-mentioned sucrose ester-based cationic lipid compounds includes the following steps:

(1) Compound A is prepared by the reaction between sucralose and compound i at a molar ratio of 1:1 to 50:

The reaction temperature is 10 to 100° C.; the reaction time is 10 to 50 h; the reaction solvents are nitrogen-containing solvent, such as N,N-dimethylformamide, pyridine, acetonitrile, piperidine and triethylamine, etc.; and the weight-to-volume ratio of the reactant to the solvent is 1:1 to 50;

In a preferred embodiment, the reaction temperature is 10 to 70° C.; the reaction time is 10 to 35 h; the reaction solvent is N,N-dimethylformamide or pyridine; the molar ratio of the sucralose to the compound of formula i is from 1:1 to 1:20. In a more preferred embodiment, the reaction temperature is 30 to 60° C.; the reaction time is 20 to 30 h; the reaction solvent is N, N-dimethylformamide or pyridine; and the molar ratio of the sucralose to the compound of formula i is from 1:1 to 1:10.

(2) Compound B is prepared by the reaction between Compound A with compound ii at a molar ratio of 1:1 to 8:

The detailed operations are indicated as follows:

a. Sucralose ester is added into a vessel, and then a certain amount of the compound of formula ii is added into the vessel, the reaction temperature is 10 to 120° C.; the reaction time is 10 to 40 h; the reaction pressure is 1.0 to 5.0 atm; the solvent is N,N-dimethylformamide (DMF), methanol, ethanol, isopropanol or isobutanol; and the weight-to-volume ratio of reactant to solvent is from 1:1 to 50;

b. After completion of the reaction, the unreacted starting material is removed by vacuum distillation, and the resulting crude product is obtained.

c. After the crude product is separated and purified by column chromatography to obtain a product, which is dissolved in a solvent and crystallized for several times to obtain a pale yellow powdery solid, which is compound B.

In a preferred embodiment, the reaction temperature is 50 to 110° C.; the reaction time is 10 to 35 h; the reaction pressure is 1.0 to 3.0 atm; the reaction solvent is DMF, ethanol or isopropanol; and the molar ratio of the compound A to the compound of formula ii is from 1:1 to 1:6. In a more preferred embodiment, the reaction temperature is 80 to 105° C.; the reaction time is 15 to 25 h; the reaction pressure is from 1.0 to 2.0 atm; the reaction solvent is ethanol or isopropanol; and the molar ratio of the compound A to the compound of formula ii is from 1:1 to 1:3.

When the synthesized product is a quaternary ammonium salt, the equilibrium anions $F^-$, $Br^-$, $I^-$ can be obtained by replacing $Cl^-$ with an ion exchange column.

In the description of the preparation method of the said sucrose ester based cationic lipid compounds, the definition of each substituent group is the same as the definition in the above-mentioned description of the compounds.

III. The sucrose ester based cationic lipid composition of the invention, the composition is consisted of the above sucrose ester based cationic lipid compound and a co-lipid. The mass ratio of the sucrose ester based cationic lipid compound to the co-lipid is from 10:1 to 1:10. In a preferred technical solution, the mass ratio of the sucrose ester based cationic lipid compound to the co-lipid is from 5:1 to 1:5. In a more preferred technical solution, the mass ratio is from 3:1 to 1:3.

The mentioned co-lipid is selected from one or two or more of lecithin, phosphatidyl ethanolamine, glycolipid, dioleoyl-sn-glycero phosphatidylchlorine (DOPC), palmitoyl-oleoyl phosphatidyl ethanolamine (POPE), dioleoyl-sn-glycero phosphatidyl ethanolamine (DOPE), cholesterol (Chol), chitosan or sucrose ester. In a preferred technical solution, the co-lipid is selected from lecithin, DOPC, DOPE, Chol, chitosan or sucrose ester, in a more preferred technical solution, the co-lipid is selected from DOPE, Chol, chitosan or sucrose ester.

The appearance of said sucrose ester based cationic composition is suspension, emulsion, micelle or liposome.

IV. The cationic lipid complexes in the invention are prepared by the sucrose ester-based cationic lipid composition and the mentioned nucleic acid, the mass ratio of the sucrose ester-based cationic lipid composition to the nucleic acid is from 20:1 to 1:20. In a preferred technical solution of the invention, the mass ratio of the sucrose ester based cationic lipid compound to the nucleic acid is from 5:1 to 1:15, more preferably the mass ratio is from 1:1 to 1:10.

The mentioned nucleic acids in the said complexes are composed one or two or more of pDNA, microRNA or siRNA.

The invention has the following advantages over the prior art:

1. In the preparation of the sucrose ester based cationic lipid compound in the invention, sucralose is used to replace sucrose as the raw material, compared with sucrose, sucralose is lack of three hydroxyls and only have one primary hydroxyl, through the esterification reaction, sucralose can react with acidic compound and produce a sucrose ester-based lipid compound with single structure. The preparation method is simple, environmentally friendly, safe, and suitable for laboratory preparation and industrialized production.

2. The sucrose ester based cationic lipid compositions (e.g., liposome) of the invention have excellent biocompatibility and degradability, of which the cytotoxicity is lower than that of currently commonly-used transfection reagents Lipofectamine 2000 and DOTAP.

3. The sucrose ester based cationic lipid compositions (e.g., liposome) of the invention are used for nucleic acid delivery, of which the transfection efficiency is superior to that of currently commonly-used transfection reagents Lipofectamine 2000 and DOTAP.

In conclusion, the sucrose ester based cationic vector prepared by the invention has the characteristics of simple preparation, low toxicity and high transfection efficiency, and has a good application prospect as a gene vector.

DETAILED DESCRIPTION OF THE INVENTION

The structure of the sucrose ester based cationic lipid compound synthesized by the above method in the invention is confirmed using nuclear magnetic resonance spectroscopy ($^1H$ NMR and $^{13}C$ NMR) or mass spectrometry.

Example 1 Preparation of Sucralose Laurate Quaternary Ammonium Salt (TSI12)

(1) Synthesis of Sucralose Laurate

In a 250 mL vessel equipped with a thermometer and a reflux tube, 3.9 g of sucralose, 3 g of anhydrous potassium carbonate, 5 mL of pyridine and N, N-dimethylformamide (DMF, 10 mL) were added followed by keeping the temperature of the oil bath at 75° C., after the full dissolution under magnetic stirring, 5 mL of lauric acid was dropwise added. After the reaction for 24 h, a pale yellow filtrate was obtained and then was subject to vacuum rotary evaporation to remove the solvent so as to obtain amber viscous oily liquid. After the column chromatographic purification, a white amorphous esterification product was obtained, of which the structure was characterized by the following: $^1H$ NMR (400 MHz, $CDCl_3$) δ: 5.44 (t, J=124.9, 2H), 6.37-4.56

(m, 6H), 6.37-4.28 (m, 10H), 6.37-3.89 (m, 20H), 6.37-3.59 (m, 26H), 6.37-2.37 (m, 28H), 2.32 (t, J=14.7, 4H), 2.07 (s, 2H), 1.99 (s, 2H), 1.77 (s, 2H), 1.74-1.58 (m, 6H), 1.42-1.15 (m, 33H), 1.52-0.58 (m, 39H), 1.43-0.58 (m, 39H), 1.11-0.53 (m, 6H). $^{13}$C NMR (400 MHz, CDCl$_3$) δ: 174.44 (s), 107.88 (s), 94.90 (s), 82.14 (s), 80.40 (s), 74.63 (s), 74.02 (s), 73.37 (s), 71.64 (s), 65.88 (s), 64.52 (s), 44.29 (s), 42.93 (s), 33.92 (s), 31.73 (s), 29.07 (t, J=7.9), 25.42 (s), 23.16 (s), 14.00 (s). ESI-MS, m/z: Found [M+3H]$^{3+}$, 581.10, [M+2H−Cl]$^+$, 545.1, C$_{24}$H$_{41}$Cl$_3$O$_9$ calcd for [M]=578.1816, [M+3H]=581.1894, [M+2H−Cl]=545.2127.

(2) Synthesis of Sucralose Laurate Quaternary Ammonium Salt

In a 250 mL vessel equipped with a N$_2$ protection, a thermometer, a reflux tube and a dropping funnel, 10 g of sucralose ester and 30 mL of N, N-dimethylformamide (DMF) were added, 30 mL of a trimethylamine solution was taken followed by keeping the temperature of the water bath at 100° C. The pressure is 1 atm. After the reaction for 24 h, the solvent was distilled off under reduced pressure. A reaction crude product was obtained which was separated and purified by column chromatography to obtain a product followed by dissolving in a solvent and crystallizing for several times to obtain a pale yellow powdery solid. The resulting solid was dried in an infrared rapid desiccator for 2 h to obtain sucralose laurate quaternary ammonium salt, of which the structure was characterized by the following: $^1$H NMR (400 MHz, CDCl$_3$) δ: 5.40-5.53 (d, 1H), 4.54-4.56 (t, 1H), 4.43 (d, 1H), [4.35 (d, 1H), 4.23 (d, 1H)], 4.28-4.30 (d, 1H), 4.30-4.33 (d, 1H), 4.10 (s, 1H), 4.07 (s, 1H), 3.95-3.99 (m, 1H), [3.84 (d, 1H), 3.65 (d, 1H)], 3.61-3.78 (d, 2H), 3.22-3.30 (s, 9H), 2.36-2.41 (t, J=7.6 Hz, 2H), 1.60-1.66 (dd, J=14.6, 8.2 Hz, 2H), 1.28-1.30 (m, J=8.9 Hz, 16H), 0.88-0.89 (t, J=6.4 Hz, 3H). $^{13}$C NMR (400 MHz, CDCl$_3$) δ: 172.97 (s), 103.57 (s), 92.22 (s), 75.12 (s), 74.94 (s), 74.44 (s), 71.14 (s), 68.03 (s), 67.43 (s), 66.91 (s), 63.53 (s), 63.06 (s), 52.94 (s), 42.93 (s), 32.95 (s), 31.05 (s), 28.19-28.72 (m), 23.99 (s), 21.71 (s), 12.43 (s). Q-TOF-MS, m/z: Found [M−Cl]$^+$, 602.2856, C$_{27}$H$_{50}$Cl$_3$NO$_9$ calcd for [M]=637.2551, [M−Cl]=602.2863.

Example 2 Preparation of Bile Acid-Sucrose Ester Based Cationic Lipid (TSB-2I)

(1) Preparation of Sucralose Bile Acid Ester

In a 250 mL vessel equipped with a thermometer and a reflux tube, 3.9 g of sucralose, 3 g of anhydrous potassium carbonate, 5 mL of acetonitrile and 20 mL of piperidine were added followed by keeping the temperature of the oil bath at 75° C., after the full dissolution under magnetic stirring, 10 mmol of bile acid was dropwise added. After the reaction was carried out for 24 h, a pale yellow filtrate was obtained which was subject to decompression rotary evaporation to remove the solvent so as to obtain amber viscous oily liquid. After the column chromatographic purification, a white amorphous mono-esterification product was obtained. $^1$H NMR (400 MHz, CDCl3) δ: 4.86-4.29 (m, 4H), 4.86-3.92 (m, 8H), 3.89-3.68 (m, 3H), 3.68-3.41 (m, 2H), 3.37-3.18 (m, 2H), 2.38 (t, J=16.1, 2H), 2.38 (t, J=16.1, 2H), 3.08-1.78 (m, 5H), 3.08-0.98 (m, 29H), 3.08-0.91 (m, 35H), 3.08-0.44 (m, 39H). $^{13}$C NMR (400 MHz, CDCl$_3$) δ: 174.51 (s), 107.88 (s), 94.90 (s), 82.14 (s), 80.40 (s), 74.63 (s), 74.09 (d), 73.56 (s), 73.37 (s), 71.64 (s), 70.69 (s), 67.02 (s), 65.88 (s), 64.52 (s), 50.15 (s), 47.48 (s), 45.82 (s), 44.29 (s), 42.93 (s), 41.84 (s), 40.62 (s), 40.36 (s), 38.98 (s), 35.64 (s), 34.24 (s), 31.84 (d, J=16.2), 30.78 (s), 29.76 (s), 29.33 (s), 28.14 (s), 24.87 (s), 18.78 (s), 17.69 (s), 11.94 (s). Q-TOF-MS, m/z: Found [M+Na]$^+$, 825.2860, C$_{36}$H$_{57}$Cl$_3$O$_{13}$ calcd for [M]=802.2865, [M+Na]=825.2865.

(2) Synthesis of Bile Acid—Sucrose Ester Based Cationic Lipid

In a 250 mL vessel equipped with a N$_2$ protection, a thermometer, a reflux tube and a dropping funnel, 5 mmol of an isopropanol (20 mL) solution of sucralose bile acid ester and 0.7 g of anhydrous potassium carbonate were added followed by keeping the temperature of water bath at 60° C. Under the magnetic stirring, 10 mmol of an ethanol (10 mL) solution of diethanolamine was dropwise added for about 1 h. After the completion of dropwise addition, the temperature of water bath rose to 100° C. The reaction was carried out for 6 h. The reaction mixture was filtered to obtain a filtrate which was subject to decompression rotary evaporation to remove the solvent so as to obtain a mixture. Finally, high-purity bile acid-sucrose ester based cationic lipid was obtained by preparative chromatographic purification. $^1$H NMR (400 MHz, CDCl$_3$) δ: 5.57 (d, J=14.8, 2H), 4.77 (d, J=14.2, 2H), 4.56-4.35 (m, 7H), 4.30-4.05 (m, 6H), 3.81-3.60 (m, 4H), 3.59-3.37 (m, 10H), 3.37-3.18 (m, 4H), 2.92-2.40 (m, 12H), 2.35 (t, J=15.7, 4H), 2.15-1.82 (m, 10H), 1.82-1.28 (m, 43H), 1.24 (s, 6H), 1.18-1.03 (m, 2H), 0.96 (s, 12H), 0.88 (d, J=12.8, 6H), 0.75-0.44 (m, 2H). $^{13}$C NMR (400 MHz, CDCl$_3$) δ: 174.51 (s), 107.88 (s), 94.90 (s), 80.40 (s), 78.39 (s), 78.09 (s), 74.09 (d), 73.56 (s), 73.37 (s), 71.64 (s), 70.69 (s), 67.02 (s), 65.88 (s), 64.52 (s), 59.18 (s), 58.37 (s), 57.48 (s), 50.15 (s), 47.48 (s), 45.82 (s), 44.29 (s), 41.84 (s), 40.62 (s), 40.36 (s), 38.98 (s), 35.64 (s), 34.24 (s), 31.84 (d), 30.78 (s), 29.76 (s), 29.33 (s), 28.14 (s), 24.87 (s), 18.78 (s), 17.69 (s), 11.94 (s). Q-TOF-MS, m/z: Found [M+Na]$^+$, 894.3891, C$_{40}$H$_{67}$Cl$_2$NO$_{15}$ calcd for [M]=871.3888, [M+Na]=994.3888.

Example 3 Preparation of Cholesterol-Sucrose Ester Based Cationic Lipid (TSD-2D)

(1) Preparation of Sucralose Cholesterol Ester

In a 250 mL vessel equipped with a thermometer and a reflux tube, 3.9 g of sucralose, 3 g of anhydrous potassium carbonate, 5 mL of trimethylamine and 20 mL of N, N-dimethylformamide (DMF) were added followed by keeping the temperature of the oil bath at 75° C. After the full dissolution under magnetic stirring, 10 mmol of cholesterol maleic acid was added. After the reaction was carried out for 24 h, a pale yellow filtrate was obtained, and was subject to decompression evaporation to remove the solvent so as to obtain amber viscous oily liquid. After column chromatographic purification, a pale yellow amorphous esterification product was obtained. $^1$H NMR (400 MHz, CDCl$_3$) δ: 6.31 (s, 4H), 4.73-4.56 (m, 6H), 4.55-4.37 (m, 6H), 4.26 (ddd, J=23.6, 19.1, 12.2, 4H), 3.79-3.57 (m, 5H), 2.66-0.61 (m, 87H), 1.82-0.61 (m, 71H), 1.73-0.88 (m, 65H), 0.82 (s, 6H). $^{13}$C NMR (400 MHz, CDCl$_3$) δ: 168.13 (s), 167.08 (s), 140.62 (s), 132.99 (s), 131.80 (s), 121.95 (s), 107.88 (s), 94.90 (s), 82.14 (s), 80.40 (s), 74.89 (s), 74.63 (s), 74.02 (s), 73.37 (s), 71.64 (s), 66.85 (s), 64.52 (s), 55.26 (s), 51.39 (s), 50.92 (s), 44.29 (s), 42.93 (s), 42.59 (s), 39.59 (s), 39.43 (s), 39.19 (s), 37.80 (s), 37.22 (s), 32.76 (d), 32.25 (s), 30.45 (s), 28.55-28.27 (m), 27.55 (s), 24.28 (s), 22.74 (s), 21.49 (s), 18.73 (s), 12.92 (s). Q-TOF-MS, m/z: Found [M+Na]$^+$, 971.3435, C$_{42}$H$_{63}$Cl$_3$O$_{11}$ calcd for [M]=848.3436, [M+Na]=971.3436.

(2) Synthesis of Cholesterol—Sucrose Ester Cationic Lipid

In a 250 mL vessel equipped with a N$_2$ protection, a thermometer, a reflux tube and a dropping funnel, 5.2 mmol of an isobutanol (20 mL) solution of sucralose cholesterol ester and 1.0 g of anhydrous potassium carbonate were added. The temperature of the water bath was kept at 60° C. Under magnetic stirring, 16.5 mmol of a methanol solution (20 ml) of diethylamine was dropwise added for about 1 h. After the dropwise addition, the temperature of the water bath rose to 100° C. After increasing the pressure to 2 atm, the reaction was carried out for 6 h. The reaction mixture was filtered to obtain a filtrate which was subject to decompression evaporation to remove isobutanol to obtain a mixture. Finally, a high-purity cholesterol-sucrose ester based cationic lipid was obtained by preparative chromatographic purification.

$^1$H NMR (400 MHz, CDCl$_3$) δ: 6.31 (s, 4H), 5.01-4.24 (m, 10H), 5.01-3.73 (m, 24H), 2.85 (ddd, J=23.3, 12.5, 6.7, 6H), 2.39 (q, J=6.3, 4H), 2.24-2.14 (m, 4H), 2.00-1.83 (m, 8H), 2.68-0.75 (m, 107H), 2.46-0.75 (m, 105H), 1.72-1.45 (m, 20H), 1.44-1.35 (m, 6H), 1.34-0.88 (m, 53H), 0.82 (s, 6H). $^{13}$C NMR (400 MHz, CDCl$_3$) δ: 168.13 (s), 167.08 (s), 140.62 (s), 132.99 (s), 131.80 (s), 121.95 (s), 107.88 (s), 94.90 (s), 80.40 (s), 78.39 (s), 78.09 (s), 74.89 (s), 74.02 (s), 73.37 (s), 71.64 (s), 66.85 (s), 64.52 (s), 58.25 (s), 55.26 (s), 51.39 (s), 50.92 (s), 48.12 (s), 44.29 (s), 42.59 (s), 39.59 (s), 39.43 (s), 39.19 (s), 37.80 (s), 37.22 (s), 32.76 (d), 32.25 (s), 30.45 (s), 28.55-28.27 (m), 27.55 (s), 24.28 (s), 22.74 (s), 21.49 (s), 18.73 (s), 12.92 (s), 12.32 (s). Q-TOF-MS, m/z: Found [M+Na]$^+$, 908.4565, C$_{46}$H$_{73}$Cl$_2$NO$_{11}$ calcd for [M]=885.4561, [M+Na]=908.4561.

Example 4 Preparation of Cationic Liposomes

The sucrose ester based cationic lipids TSI12, TSB-2I, TSD-2D, TSI14 (sucralose myristate quaternary ammonium salt) and TSI16 (sucralose palmitate quaternary ammonium salt) obtained in the above Examples 1, 2 and 3 were irradiated under a UV light for 1 h. 1 mg of a cationic lipid and a certain amount of DOPE (the molar ratios of cationic lipid to DOPE were 2:1, 1:1 and 1:2) or cholesterol Chol, (the molar ratios of cationic lipid to Chol were 5:1, 4:1, 3:1, 2:1 and 1:1) were added to 1 mL of chloroform to be dissolved completely followed by blow-dry with the uniform nitrogen stream to form a thin film. The resulting film was dried in vacuum for 10 h, and the organic solvent was cleaned up. 1 mL of sterile deionized water was added. At a constant temperature of 55° C., the mixture was subject to ultrasound for 1-3 h until clear clarification so as to prepare cationic liposomes with a final concentration of 1.00 mM.

Figure 4:
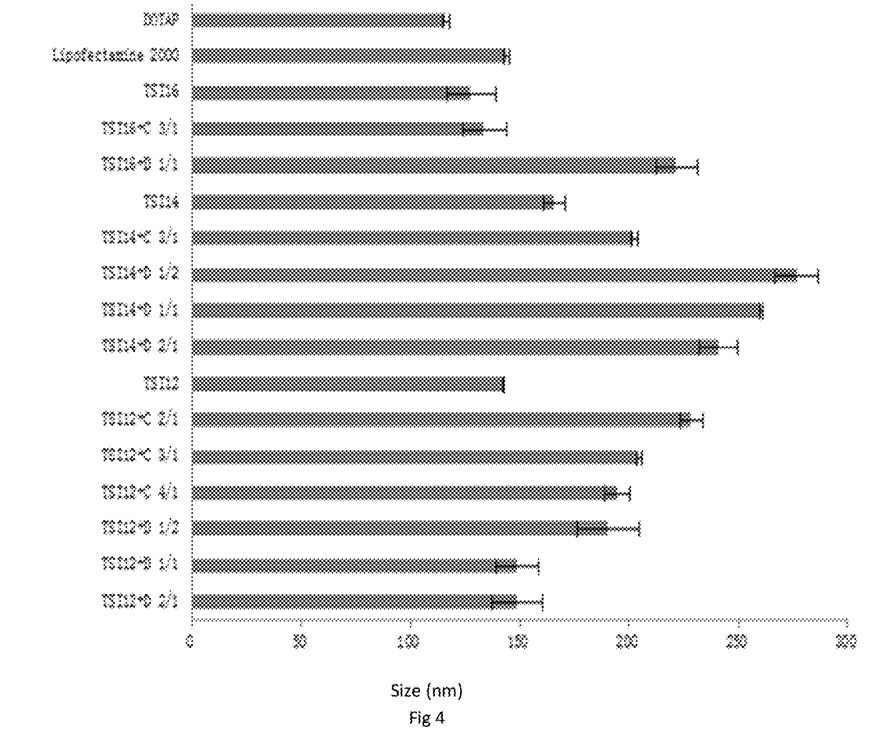
FIG. 4 is the particle size diagram of the cationic liposome of Example 5.
Figure 5:
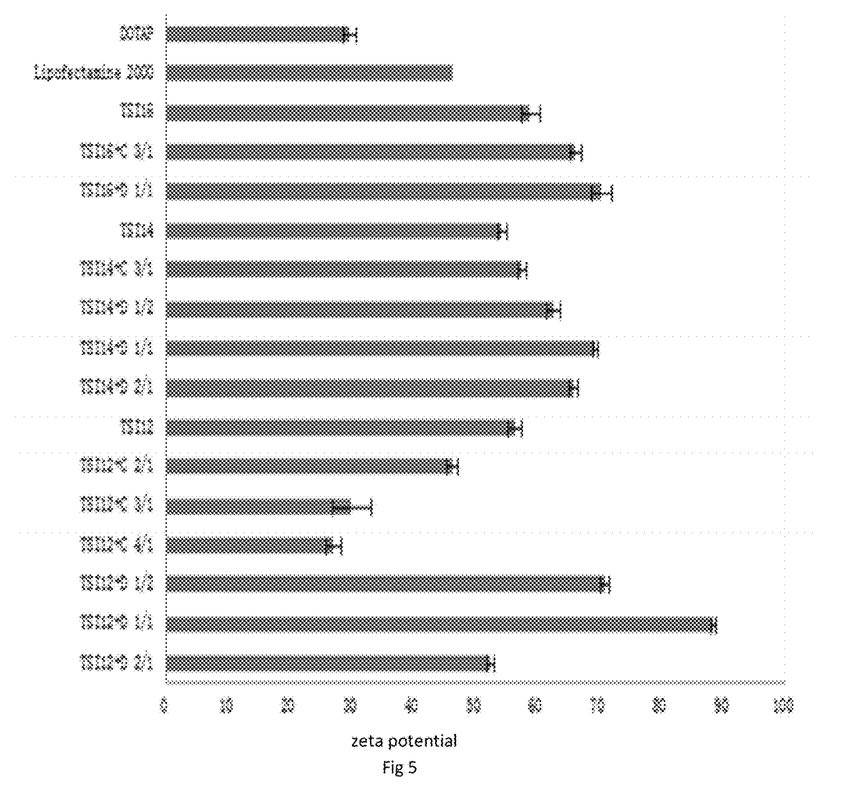
FIG. 5 is the zeta potential diagram of the cationic liposome of Example 5.

Example 5 Determination of Particle Size and Zeta Potential of Cationic Liposomes Approximately 20 μL of the cationic liposomes prepared in Example 4 was taken and added to about 1 mL of water. The particle size and distribution of the cationic liposomes were measured using a Zeta-sizer-1000 laser particle size analyzer (Japan, HORIBA Scientific Company, the optical maser wavelength of 630 nm and the scattering angle of 90° to 173°), and the results were shown in FIG. 4. The zeta potential of the cationic liposomes was measured using a Zetaplus ζ-potential analyzer (HORIBA Scientific Company, Japan), and the results were shown in FIG. 5. In FIG. 4 and FIG. 5, Lipofectamine 2000 (Invitrogen Company, USA) and DOTAP (N-(2,3-dioleooyloxy-1-propyl) trimethylmethanesulfonate ammonia, Roche Company, Switzerland) are the commonly used cationic liposome in this field. The results in FIG. 4 show that the liposomes of the invention have a particle size in the range of 100 to 350 nm, and the particle size range falls within the effective transfection particle size range (<1 μm). The results in FIG. 5 show that the zeta potential of the liposomes of the invention is between 25 and 90 mV; the Zeta potential of the commercial reagent DOTAP is 29.8 mV and the Zeta potential of Lipofectamine 2000 is 46.4 mV; and they have an ability to bind to negatively charged ions (including nucleic acid and other molecules).

Example 6 Preparation of Liposome-DNA Complexes

Firstly, a certain amount of plasmid DNA (pGFP-N2 or pGL-3) was diluted in DMEM to prepare a 25 μL system. A certain volume of the cationic liposomes with a concentration of 1 mg/mL prepared in Example 4 was diluted in DMEM to prepare a 25 μL system, and then 25 μL of a liposome diluent was dropwise added to 25 μL of the plasmid DNA diluent so that the mass ratios (μg/μg) of liposome to DNA were 1:1, 2:1, 3:1, 4:1, 6:1, 8:1 and 10:1, respectively. The resulting mixture was mixed thoroughly with a vortex oscillator and was incubated at room temperature for 20 mins to form 50 μL of liposome-DNA complexes.

Example 7 Detection of the Binding Capacity of Cationic Liposomes to DNA

Figure 6:
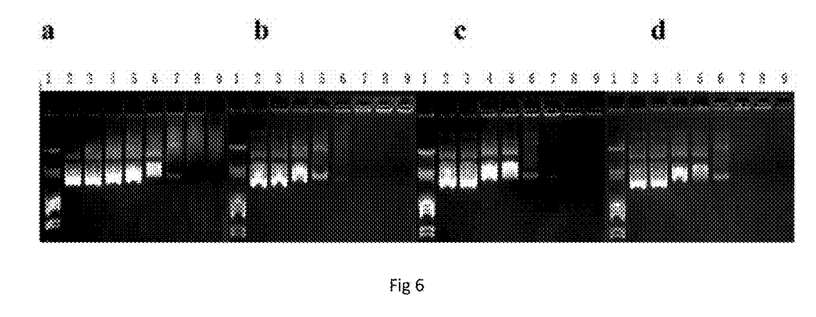
FIG. 6 is the electrophoretogram of the cationic liposome-DNA complex of Example 7.

20 μL of the complex solution prepared in Example 6 was uniformly mixed with 1.6 μL of loading buffer (Takara Company, Japan) followed by addition into 1.2% agarose gel. The mixture was electrophoresed at 90 V for 1 h. The DNA electrophoretogram was observed and photographed in a gel imaging system, as shown in FIG. 6. FIG. 6a shows the result of measurement of the DNA binding ability of an individual TSI14 liposome. FIGS. 6b, 6c and 6d show the results of measurement of the DNA binding ability of liposomes prepared by mixing TSI14 with DOPE at 2:1, 1:1 and 1:2, respectively.

FIGS. 6a, 6b, 6c and 6d: the first lane was a 2 kb DNA marker (λDNA/EcoR I+Hind III Markers, purchased from SABC); the second lane was naked DNA; and the 3th-10th lanes were liposome-DNA complexes in which the ratios of liposome to DNA were 1:1, 2:1, 3:1, 4:1, 6:1, 8:1 and 10:1, respectively. Without the addition of liposomes (naked DNA), a typical plasmid band appeared. After the addition of liposomes, the DNA band was significantly weakened. With the increase of the added amount of liposomes, the delay ability of DNA was obviously enhanced. It showed that the liposomes prepared by the invention had the capability of binding DNA.

Example 8 Determination of Transfection Efficiency

The liposome-DNA complex prepared in Example 6 was taken to carry out a condition experiment in a cell line Hep-2 (human laryngeal carcinoma epithelial cells) to investigate the transfection efficiency under different conditions and to optimize the use conditions of the reagent.

The cells were planted on a 96-well cell culture plate. An appropriate amount of cells is planted in each well, and the total volume of a cell culture fluid (comprising serum and antibiotics) was 100 μL. The cells were placed into an incubator with 5% of CO$_2$ at a temperature of 37° C. for 24 h to achieve a cell density of 1 to 1.5×10$^4$ on the day of transfection.

The growth medium was removed and was replaced with a medium with the equivalent amount (100 μL, without serum and antibiotics). 50 μL of the liposome-DNA complex sample of Example 6 was directly added into the plate wells, with 3 parallel wells per sample, followed by shaking the culture plate and gently mixing. The culture medium was cultivated in an incubator with 5% of $CO_2$ at a temperature of 37° C. for 5 h, and was replaced with a medium containing serum and antibiotics. After incubation for 48 h, the gene expression analysis was carried out.

Gene Expression Analysis:

(1) Green fluorescent protein detection: The green fluorescent protein signal was observed by an inverted fluorescence microscope. Positive cells emitted bright green fluorescence, while negative cells failed. The results were shown in FIG. 7.

(2) Luciferase detection: The sample was firstly washed with PBS for 3 times, and then 100 μL of lysis buffer was added into each well. Lysate was collected, and was centrifuged at 12000 rpm and 4° C. for 5 min. 20 μL of supernatant was used for detecting the activity of luciferase. The relative light unit (RUL) value was detected on the Luminometer by a luciferase detection reagent. The luminescence time was measured to be 10 s. The results were shown in FIG. 8.

Figure 7:
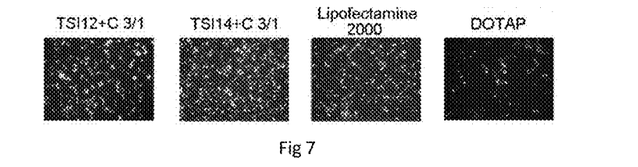
FIG. 7 is the graph showing the result of the green fluorescent protein detection after the Hep-2 cell is transfected by the cationic liposome-DNA complex in Example 8.
Figure 8:
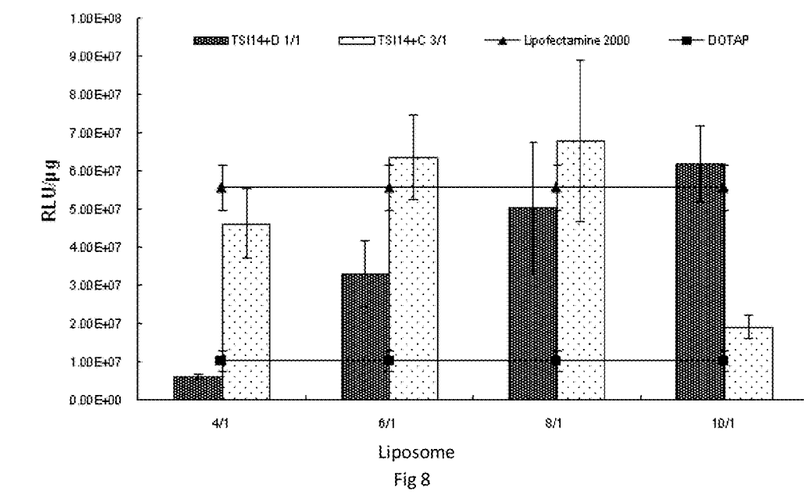
FIG. 8 is the graph showing the result of the luciferase assay after the Hep-2 cell is transfected by the cationic liposome-DNA complex in Example 8.

Experimental results were shown in FIGS. 7 and 8. The liposomes prepared according to the invention have the ability of delivering DNA. Wherein when the ratios of the liposome TSI14+C 3/1 to DNA were 6/1 and 8/1, and the ratio of the liposome TSI14+D 1/1 to DNA was 10/1, the transfection efficiency was higher than that of the commercial reagents Lipofectamine2000 and DOTAP.

Example 9 Determination of MTT Toxicity

Figure 9:
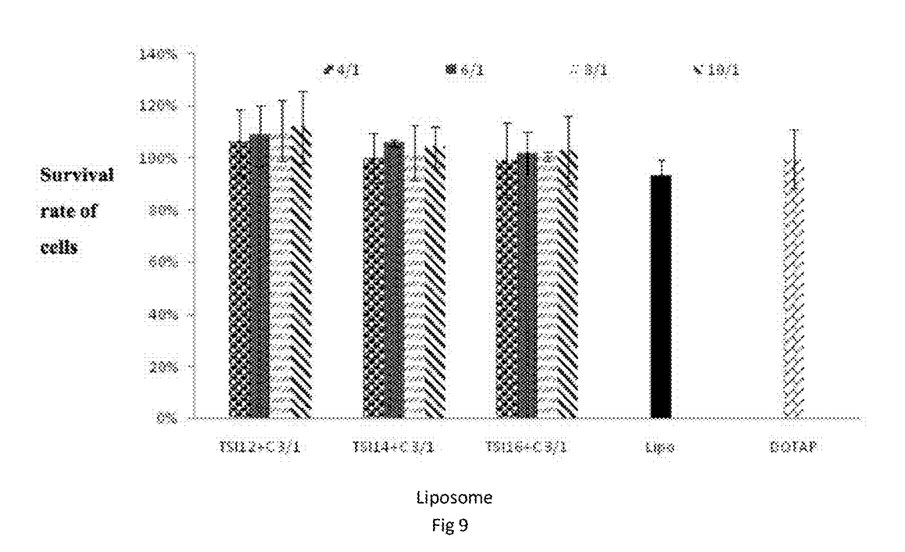
FIG. 9 is the Hep-2 cell viability diagram using the MTT assay in Example 9.

Hep-2 (human laryngeal carcinoma epithelial cells) was planted on a 96-well cell culture plate, and 3 wells were parallel and averaged. $1.5 \times 10^4$ Cells/100 μL of a culture solution were seeded in each well and were incubated to 90% confluency under the environment of 37° C. and 5% of $CO_2$. The medium was removed followed by washing with D-Hanks once. 0.5 μg of the plasmid DNA (pGFP-N2) and the transfection reagent were diluted in 25 μL of DMEM, respectively, and then the liposome-DNA complex prepared in Example 6 was added to a 96-well cell culture plate. Similarly, the complex of Lipofectamine 2000 (Lipo) (its mass ratio to plasmid was 3:1) and DOTAP (its mass ratio to plasmid was 6:1) was added as a positive control into a 96-well cell culture plate. 100 μL of the medium free of cationic liposomes (without serum and antibiotics) was used as a negative control. The culture medium continued to be incubated in an incubator with 5% of carbon dioxide at 37° C. After 24 h, 20 μL, of 3-(4,5-dimethylthiazol-2)-2,5-diphenyltetrazolium bromide (MTT) solution (5 mg/mL in PBS, pH 7.4) was added into each well and continued to be incubated for 5 h, followed by removing the medium. The resulting formazan crystals were dissolved with 150 μL of dimethylsulfoxide (DMSO) and a vigorous mixing rendered formazan dissolved. The reading was taken in a microplate reader, and the absorption wavelength was 570 nm. The microplate reader was adjusted to zero with a cell-free medium. The relative viability of the cationic liposomes relative to the control cells was calculated according to the following formula:

$$[A]_{Sample}/[A]_{Control} \times 100$$

$[A]_{Sample}$ is a light absorption value of the test well, and $[A]_{Control}$ is a light absorption value of the negative control well.

Experimental results were shown in FIG. 9. The cell viability of the sucrose ester based cationic liposomes prepared in the invention in Hep-2 cells was generally higher than that of the commercial reagents Lipofectamine 2000 and DOTAP.

Example 10 Preparation of Cationic Micelles 1 mg of TSD-2D, and a certain amount of sucrose ester (the molar ratios of cationic lipid to sucrose ester were 2:1, 1:1 and 1:2), chitosan (the molar ratios of cationic lipid to chitosan were 2:1, 1:1 and 1:2) or palmitoyl oleoylphosphatidylethanolamine (the molar ratios of cationic lipid to palmitoyl oleoylphosphatidylethanolamine were 5:1, 4:1, 3:1, 2:1 and 1:1) were added and dissolved in DMF to prepare a solution at a concentration of 1 mg/mL. The deionized water was added dropwise under vigorous stirring until the solution became slightly cloudy to obtain a stable micellar solution. It was transferred to a dialysis bag and was placed in deionized water for dialysis during which the deionized water was replaced for several times. After 3 days, an aqueous solution with a certain concentration of 1 mg/mL was formulated.

Example 11 Preparation of Micelle-siRNA Complexes

Firstly, a certain amount of siRNA was diluted in DMEM to prepare a 25 μL system. A certain volume of the cationic micelles with a concentration of 1 mg/mL prepared in Example 10 were further diluted in DMEM to prepare a 25 μL system. Then 25 μL of the micelle diluent was added dropwise into 25 μL of the diluent of the plasmid DNA, so that the mass ratios (μg/μg) of the micelles to the siRNA were 1:1, 2:1, 3:1, 4:1, 6:1, 8:1 and 10:1, respectively. The mixture was fully mixed with a vortex oscillator and was incubated at room temperature for 20 min to form 50 μL of micelle-siRNA complexes.

Example 12 Detection of the Binding Ability of Cationic Micelles to siRNA

20 μL of the micelle-siRNA complex solution prepared in Example 11 was mixed well with 1.6 μL of loading buffer (Takara Company, Japan). The mixture was added to 1.2% agarose gel, and was electrophoresed at 90 V for 1 h. The siRNA electrophoretogram was observed and photographed in a gel imaging system.

The invention claimed is:
1. A sucrose ester based cationic lipid compound having a structure of a general formula I:

I

R is $C_{10-20}$ hydroxyl, a bile acid group or a cholesterol ester group;

Y is —NR$^a$R$^b$ or —N$^+$R$^a$R$^b$R$^c$X$^-$, wherein R$^a$, R$^b$ and R$^c$ are the same or different, and are hydrogen, C$_{1-6}$ hydroxyl, C$_{1-6}$ hydroxyalkyl, galactosyl, mannosyl and/or a folic acid ester group; X$^-$ is F$^-$, Cl$^-$, Br$^-$, or I$^-$.

2. A method for preparing the sucrose ester based cationic lipid compound according to claim 1, the method comprising the following steps:

(1) preparing a Compound A by the reaction between sucralose and a compound according to formula i at a molar ratio of 1:1~50:

Sucralose                i

Compound A the reaction temperature is 10 to 100° C., the reaction time is 10 to 50 h, the reaction solvent is a nitrogen-containing solvent, and a weight-to-volume ratio of the reactant to the solvent is from 1:1 to 50;

the compound of formula i is selected from C$_{10-20}$ hydroxyl acid, bile acid or cholesterol derivative (cholesterol acid);

(2) preparing a Compound B corresponding to the general formula I by the reaction between the compound A with a compound according to formula ii at a molar ratio of 1:1 to 8:

Compound A ii                Compound B the reaction temperature is 10 to 120° C., the reaction time is 10 to 40 h, the reaction pressure is 1.0 to 5.0 atm, the solvent is N, N-dimethylformamide, methanol, ethanol, isopropanol or isobutanol, and a weight-to-volume ratio of the reactant to the solvent is from 1:1 to 50;

R is C$_{10-20}$ hydroxyl, a bile acid group or a cholesterol ester group;

R$^a$, R$^b$ and R$^c$ of the compound of formula ii are the same or different, and are hydrogen, C$_{1-6}$ hydroxyl, C$_{1-6}$ hydroxyalkyl, galactosyl, mannosyl and/or folic acid ester group, Y of the Compound B is —NR$^a$R$^b$ or —N$^+$R$^a$R$^b$R$^c$X; X$^-$ is F$^-$, Cl$^-$, Br$^-$, I$^-$.

3. The method for preparing the sucrose ester based cationic lipid compound according to claim 2, wherein when the synthesized product is a quaternary ammonium salt, equilibrium anions F$^-$, Br$^-$ and I$^-$ can be obtained by replacing Cl$^-$ with an ion exchange column.

4. A cationic lipid composition consisting of the sucrose ester based cationic lipid compound according to claim 1 and a co-lipid, wherein a mass ratio of the said sucrose ester cationic lipid compound to the co-lipid is from 10:1 to 1:10.

5. The cationic lipid composition according to claim 4, wherein the co-lipid is one or a mixture of two or more of lecithin, phosphatidylethanolamine, glycolipid, dioleoylphosphatidyl chloride, palmitoyl oleoylphosphatidylethanolamine, dioleoylphosphatidylethanolamine, cholesterol, chitosan and sucrose ester.

6. The cationic lipid composition according to claim 4, wherein the composition is one or a mixture of two or more of suspension, emulsion, micelle or liposome.

7. A cationic lipid complex consisting of the cationic lipid composition according to claim 4 combined with nucleic acid, wherein a mass ratio of the cationic lipid composition to the nucleic acid is from 20:1 to 1:20.

8. The cationic lipid complex according to claim 7, wherein the nucleic acid delivered is one or a mixture of two or more of pDNA, microRNA and siRNA.

* * * * *